(12) United States Patent
Firooznia

(10) Patent No.: US 7,713,991 B2
(45) Date of Patent: *May 11, 2010

(54) IMIDAZO[[1, 5-A] PYRIDINE DERIVATIVES AND METHODS FOR TREATING ALDOSTERONE MEDIATED DISEASES

(75) Inventor: Fariborz Firooznia, Florham Park, NJ (US)

(73) Assignee: Novartis AG, Basel (CH)

( * ) Notice: Subject to any disclaimer, the term of this patent is extended or adjusted under 35 U.S.C. 154(b) by 284 days.

This patent is subject to a terminal disclaimer.

(21) Appl. No.: 11/739,290

(22) Filed: Apr. 24, 2007

(65) Prior Publication Data

US 2007/0197582 A1 Aug. 23, 2007

Related U.S. Application Data

(63) Continuation of application No. 10/534,631, filed as application No. PCT/EP03/12851 on Nov. 17, 2003, now Pat. No. 7,223,866.

(51) Int. Cl.
*A01N 43/42* (2006.01)
*A61K 31/44* (2006.01)

(52) U.S. Cl. .................................................... 514/300
(58) Field of Classification Search ................... 514/300
See application file for complete search history.

(56) References Cited

U.S. PATENT DOCUMENTS

| | | | |
|---|---|---|---|
| 4,588,732 A | 5/1986 | Browne | |
| 4,617,307 A | 10/1986 | Browne | |
| 4,889,861 A | 12/1989 | Browne | |
| 5,529,992 A | 6/1996 | Weber | |
| 6,037,349 A | 3/2000 | Sombroek et al. | |
| 6,150,347 A | 11/2000 | Weber | |

FOREIGN PATENT DOCUMENTS

JP 09071586 11/2002

WO WO 01/27107 4/2001

OTHER PUBLICATIONS

Takeda et al., Hypertension, (Oct. 2000) vol. 36, No. 4, pp. 495-500.*
Browne, L.J. et al., "Fadrozole Hydrochloride: A Potent, Selective, Nonsteroidal Inhibitor of Aromatase for the Treatment of Estrogen-Dependent Disease," J. Med. Chem. vol. 34, 1991, pp. 725-736, (1991).

* cited by examiner

*Primary Examiner*—D. Margaret Seaman
*Assistant Examiner*—Niloofar Rahmani
(74) *Attorney, Agent, or Firm*—Sophie Binet Cross

(57) ABSTRACT

Compounds of the formula (I)

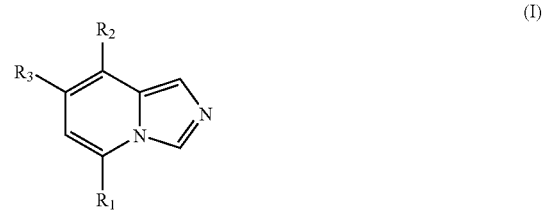

provide pharmacological agents which are inhibitors of the P450 enzyme, aldosterone synthase, and thus may be employed for the treatment of aldosterone mediated conditions. Accordingly, the compounds of formula (I) may be employed for prevention, delay of progression, or treatment of hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction. Preferred are the compounds of formula (I) which are selective inhibitors of aldosterone synthase devoid of undesirable side effects due to general inhibition of cytochrome P450 enzymes.

8 Claims, No Drawings

IMIDAZO[[1, 5-A] PYRIDINE DERIVATIVES AND METHODS FOR TREATING ALDOSTERONE MEDIATED DISEASES

This application is a continuation of U.S. application Ser. No. 10/534,631, filed Aug. 31, 2005 now U.S. Pat. No. 7,223,866, which is a 371 of International Application No. PCT/EP2003/12851, filed Nov.17, 2003.

The present invention provides compounds of the formula (I)

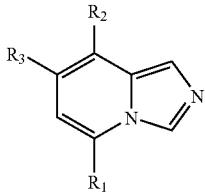

wherein
R₁ is cycloalkyl, heterocyclyl or an aryl radical of the formula

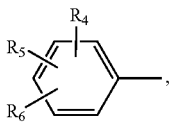

in which
R₄ is cycloalkyl, aryl or heterocyclyl; or
R₄ is optionally substituted alkyl, alkoxy, hydroxy, halogen or trifluoromethyl provided that both R₅ and R₆ are not hydrogen;
R₅ is hydrogen, halogen, cyano, alkoxy or trifluoromethyl; or
R₄ and R₅ combined together with the carbon atoms to which they are attached form an optionally substituted aromatic or heteroaromatic 5- or 6-membered ring provided that R₄ and R₅ are attached to carbon atoms adjacent to each other; or
R₄ and R₅ combined are alkylene which taken together with the carbon atoms to which they are attached form a 4- to 7-membered ring provided that R₄ and R₅ are attached to carbon atoms adjacent to each other;
R₆ is hydrogen, halogen, cyano, nitro, trifluoromethyl, optionally substituted lower alkyl, optionally substituted amino, alkoxy, carboxy, alkoxycarbonyl, sulfonyl or carbamoyl;
R₂ and R₃ are, independently, hydrogen, trifluoromethyl or alkoxy; or
R₂ and R₃ combined together with the carbon atoms to which they are attached form an optionally substituted aromatic or heteroaromatic 5- or 6-membered ring; or
R₂ and R₃ combined are alkylene which taken together with the carbon atoms to which they are attached form a 4- to 7-membered ring;

or a pharmaceutically acceptable salt thereof.

Structurally related compounds were described in the U.S. Pat. Nos. 4,588,732 and 4,617,307 respectively as thromboxane synthase inhibitors and aromatase inhibitors. The U.S. Pat. No. 6,037,349 described imidazopyridines different in its basic structure from the present compounds as having antagonistic properties towards angiotensin II.

The compounds of the present invention are inhibitors of the P450 enzyme, aldosterone synthase, and thus may be employed for the treatment of aldosterone mediated conditions. Accordingly, the compounds of formula (I) may be employed for prevention, delay of progression, or treatment of hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction. Preferred are the compounds of formula (I) which are selective inhibitors of aldosterone synthase devoid of undesirable side effects due to general inhibition of cytochrome P450 enzymes.

Listed below are definitions of various terms used to describe the compounds of the present invention. These definitions apply to the terms as they are used throughout the specification unless they are otherwise limited in specific instances either individually or as part of a larger group.

The term "optionally substituted alkyl" refers to unsubstituted or substituted straight- or branched-chain hydrocarbon groups having 1-20 carbon atoms, preferably 1-7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, cycloalkyl, acyl, alkoxy, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, carboxy, alkoxycarbonyl, alkenyl, alkynyl, aryloxy, aralkoxy, guanidino, heterocyclyl including indolyl, imidazolyl, furyl, thienyl, thiazolyl, pyrrolidyl, pyridyl, pyrimidyl, piperidyl, morpholinyl and the like.

The term "lower alkyl" refers to those optionally substituted alkyl groups as described above having 1-7, preferably 1-4 carbon atoms.

The term "halogen" or "halo" refers to fluorine, chlorine, bromine and iodine.

The term "alkenyl" refers to any of the above alkyl groups having at least two carbon atoms and further containing a carbon to carbon double bond at the point of attachment. Groups having 2-4 carbon atoms are preferred.

The term "alkynyl" refers to any of the above alkyl groups having at least two carbon atoms and further containing a carbon to carbon triple bond at the point of attachment. Groups having 2-4 carbon atoms are preferred.

The term "alkylene" refers to a straight-chain bridge of 2-5 carbon atoms connected by single bonds, e.g., —(CH₂)ₓ—, wherein x is 2-5, which may be interrupted with one or more heteroatoms selected from O, S, S(O), S(O)₂ or NR, wherein R may be hydrogen, alkyl, cycloalkyl, aryl, acyl, carbamoyl, sulfonyl, sulfamoyl, alkoxycarbonyl, aryloxycarbonyl or aralkoxycarbonyl, and the alkylene may be substituted with one or more substituents selected from alkyl, cycloalkyl, oxo, halogen, hydroxy, carboxy, alkoxy, alkoxycarbonyl and the like.

The term "cycloalkyl" refers to optionally substituted monocyclic, bicyclic or tricyclic hydrocarbon groups of 3-12 carbon atoms, each of which may be substituted by one or more substituents, such as alkyl, halo, oxo, hydroxy, alkoxy, alkanoyl, acylamino, carbamoyl, alkylamino, dialkylamino, thiol, alkylthio, nitro, cyano, carboxy, alkoxycarbonyl, sulfonyl, sulfonamido, sulfamoyl, heterocyclyl and the like.

Exemplary monocyclic hydrocarbon groups include, but are not limited to, cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.

The term "alkanoyl" refers to alkyl-C(O)—.

The term "alkanoyloxy" refers to alkyl-C(O)—O—.

The terms "alkylamino" and "dialkylamino" refer to alkyl-NH— and (alkyl)$_2$N—, respectively.

The term "alkanoylamino" refers to alkyl-C(O)—NH—.

The term "alkylthio" refers to alkyl-S—.

The term "alkylthiono" refers to alkyl-S(O)—.

The term "alkylsulfonyl" refers to alkyl-S(O)$_2$—.

The term "alkoxycarbonyl" refers to alkyl-O—C(O)—.

The term "alkoxycarbonyloxy" refers to alkyl-O—C(O)O—.

The term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.

The term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.

The term "sulfonamido" refers to alkyl-S(O)$_2$—NH—, aryl-S(O)$_2$—NH—, aralkyl-S(O)$_2$—NH—, heteroaryl-S(O)$_2$—NH—, heteroaralkyl-S(O)$_2$—NH—, alkyl-S(O)$_2$—N(alkyl)-, aryl-S(O)$_2$—N(alkyl)-, aralkyl-S(O)$_2$—N(alkyl)-, heteroaryl-S(O)$_2$—N(alkyl)-, heteroaralkyl-S(O)$_2$—N(alkyl)- and the like.

The term "sulfonyl" refers to alkylsulfonyl, arylsulfonyl, heteroarylsulfonyl, aralkylsulfonyl, heteroaralkylsulfonyl and the like.

The term "optionally substituted amino" refers to a primary or secondary amino group which may optionally be substituted by a substituent, such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carbamoyl and the like.

The term "aryl" refers to monocyclic or bicyclic aromatic hydrocarbon groups having 6-12 carbon atoms in the ring portion, such as phenyl, biphenyl, naphthyl or tetrahydronaphthyl, each of which may optionally be substituted by 1-4 substituents, such as optionally substituted alkyl, trifluoromethyl, cycloalkyl, halo, hydroxy, alkoxy, acyl, alkanoyloxy, aryloxy, optionally substituted amino, thiol, alkylthio, arylthio, nitro, cyano, carboxy, alkoxycarbonyl, carbamoyl, alkylthiono, sulfonyl, sulfonamido, heterocyclyl and the like.

The term "monocyclic aryl" refers to optionally substituted phenyl as described under aryl.

The term "aralkyl" refers to an aryl group bonded directly through an alkyl group, such as benzyl and phenethyl.

The term "aralkanoyl" refers to aralkyl-C(O)—.

The term "aralkylthio" refers to aralkyl-S—.

The term "aralkoxy" refers to an aryl group bonded directly through an alkoxy group.

The term "arylsulfonyl" refers to aryl-S(O)$_2$—.

The term "arylthio" refers to aryl-S—.

The term "aroyl" refers to aryl-C(O)—.

The term "aroyloxy" refers to aryl-C(O)—O—.

The term "aroylamino" refers to aryl-C(O)—NH—.

The term "aryloxycarbonyl" refers to aryl-O—C(O)—.

The term "heterocyclyl" or "heterocyclo" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also be optionally oxidized. The heterocyclic group may be attached at a carbon atom, or it may be attached through a nitrogen atom provided that an appropriately hybridized nitrogen atom constitutes part of the structure. In the case of bicyclic benzofused heterocyclic groups, the point of attachment is always at the ring containing at least one heteroatom as defined herein above.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroindolyl, benzothiazolyl, benzoxazinyl, benzoxazolyl, benzothienyl, benzothiazinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl, e.g., furo[2,3-c]pyridinyl, furo[3,2-b]-pyridinyl and furo[2,3-b]pyridinyl, dihydroisoindolyl, 1,3-dioxo-1,3-dihydroisoindol-2-yl, dihydroquinazolinyl, e.g., 3,4-dihydro-4-oxo-quinazolinyl, phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups substituted with 1, 2 or 3 substitutents selected from the group consisting of the following:

(a) alkyl;
(b) hydroxy (or protected hydroxy);
(c) halo;
(d) oxo, i.e., =O;
(e) optionally substituted amino, alkylamino or dialkylamino;
(f) alkoxy;
(g) cycloalkyl;
(h) carboxy;
(i) heterocyclooxy;
(j) alkoxycarbonyl, such as unsubstituted lower alkoxycarbonyl;
(k) mercapto;
(l) nitro;
(m) cyano;
(n) sulfamoyl or sulfonamido;
(o) aryl;
(p) alkanoyloxy;

(q) aroyloxy;
(r) arylthio;
(s) aryloxy;
(t) alkylthio;
(u) formyl;
(v) carbamoyl;
(w) aralkyl; or
(x) aryl substituted with alkyl, cycloalkyl, alkoxy, hydroxy, amino, acylamino, alkylamino, dialkylamino or halo.

The term "heterocyclooxy" denotes a heterocyclic group bonded through an oxygen bridge.

The term "heteroaryl" refers to an aromatic heterocycle, e.g., monocyclic or bicyclic aryl, such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like, optionally substituted by, e.g., lower alkyl, lower alkoxy or halo.

The term "heteroarylsulfonyl" refers to heteroaryl-S(O)$_2$—.

The term "heteroaroyl" refers to heteroaryl-C(O)—.

The term "heteroaroylamino" refers to heteroaryl-C(O)NH—.

The term "heteroaralkyl" refers to a heteroaryl group bonded through an alkyl group.

The term "heteroaralkanoyl" refers to heteroaralkyl-C(O)—.

The term "heteroaralkanoylamino" refers to heteroaralkyl-C(O)NH—.

The term "acyl" refers to alkanoyl, aroyl, heteroaroyl, aralkanoyl, heteroaralkanoyl and the like.

The term "acylamino" refers to alkanoylamino, aroylamino, heteroaroylamino, aralkanoylamino, heteroaralkanoylamino and the like.

Pharmaceutically acceptable salts of any compound of the present invention refer, in particular, to salts formed with acids, namely acid addition salts with the imidazolyl moiety of the structure. The acid addition salts may be formed with mineral acids, organic carboxylic acids or organic sulfonic acids, e.g., hydrochloric acid, maleic acid and methanesulfonic acid, respectively.

Similarly, salts formed with bases, e.g., cationic salts, such as alkali and alkaline earth metal salts, such as sodium, lithium, potassium, calcium, magnesium, as well as ammonium salts, such as ammonium, trimethylammonium, diethylammonium and tris(hydroxymethyl)methylammonium salts and salts with amino acids, are possible if an acidic group constitutes part of the structure.

The present invention provides bicyclic imidazole derivatives of formula (I), pharmaceutical compositions containing them, methods for preparing said compounds, and methods of treating aldosterone mediated conditions by administration of a therapeutically effective amount of a compound of the present invention or a pharmaceutical composition thereof.

Preferred are the compounds of formula (I), wherein
$R_1$ is heterocyclyl;
$R_2$ and $R_3$ are hydrogen;

or pharmaceutically acceptable salt thereof.

Preferred are also the compounds of formula (I) having the formula (IA)

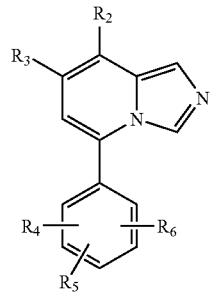

(IA)

wherein
$R_2$ and $R_3$ are, independently, hydrogen, trifluoromethyl or alkoxy; or
$R_2$ and $R_3$ combined together with the carbon atoms to which they are attached form an optionally substituted aromatic or heteroaromatic 5- or 6-membered ring; or
$R_2$ and $R_3$ combined are alkylene which taken together with the carbon atoms to which they are attached form a 4- to 7-membered ring;
$R_4$ is cycloalkyl, aryl or heterocyclyl; or
$R_4$ is optionally substituted alkyl, alkoxy, hydroxy, halogen or trifluoromethyl provided that both $R_5$ and $R_6$ are not hydrogen;
$R_5$ is hydrogen, halogen, cyano, alkoxy or trifluoromethyl; or
$R_4$ and $R_5$ combined together with the carbon atoms to which they are attached form an optionally substituted aromatic or heteroaromatic 5- or 6-membered ring provided that $R_4$ and $R_5$ are attached to carbon atoms adjacent to each other;
$R_6$ is hydrogen, halogen, cyano, nitro, trifluoromethyl, optionally substituted lower alkyl, optionally substituted amino, alkoxy, carboxy, alkoxycarbonyl, sulfonyl or carbamoyl;

or a pharmaceutically acceptable salt thereof.

Preferred are the compounds of formula (IA) having the formula (IB)

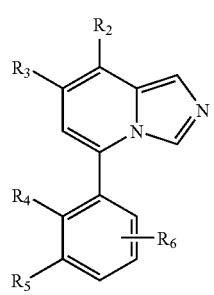

(IB)

wherein
$R_2$ and $R_3$ are, independently, hydrogen, trifluoromethyl or alkoxy; or
$R_2$ and $R_3$ combined together with the carbon atoms to which they are attached form aromatic or heteroaromatic 5- to 6-membered ring;
$R_4$ is cycloalkyl, aryl or heterocyclyl; or $R_4$ is hydroxy, halogen or trifluoromethyl provided that both $R_5$ and $R_6$ are not hydrogen;

$R_5$ is hydrogen, halogen, cyano, alkoxy or trifluoromethyl; or $R_4$ and $R_5$ combined together with the carbon atoms to which they are attached form an optionally substituted aromatic or heteroaromatic 5- or 6-membered ring;

$R_6$ is hydrogen, halogen, cyano, nitro, trifluoromethyl, optionally substituted lower alkyl, optionally substituted amino, alkoxy, carboxy, alkoxycarbonyl, sulfonyl or carbamoyl;

or a pharmaceutically acceptable salt thereof.

Preferred are compounds of formula (IB), wherein
$R_2$ and $R_3$ are hydrogen;

or a pharmaceutically acceptable salt thereof.

Preferred are also compounds of formula (IB), wherein
$R_4$ is monocyclic aryl or heteroaryl;
$R_5$ is hydrogen;
$R_6$ is hydrogen, halogen, cyano, trifluoromethyl or alkoxy;

or a pharmaceutically acceptable salt thereof.

Preferred are also compounds of formula (IB), wherein
$R_4$ and $R_5$ combined together with the carbon atoms to which they are attached form an optionally substituted aromatic or heteroaromatic 5- or 6-membered ring;
$R_6$ is hydrogen, halogen, cyano, trifluoromethyl or alkoxy;

or a pharmaceutically acceptable salt thereof.

Particular embodiments of the invention are:
5-Naphthalen-1-yl-imidazo[1,5-a]pyridine;
5-Biphenyl-4-yl-imidazo[1,5-a]pyridine;
5-Biphenyl-2-yl-imidazo[1,5-a]pyridine;
5-Benzofuran-3-yl-imidazo[1,5-a]pyridine; and
4-Imidazo[1,5-a]pyridin-5-yl-3,6-dihydro-2H-pyridine-1-carboxylic acid benzyl ester;

or a pharmaceutically acceptable salt thereof.

The compounds of the invention depending on the nature of the substituents, may possess one or more asymmetric centers. The resulting diastereoisomers, enantiomers and geometric isomers, and mixtures thereof, are encompassed by the instant invention.

Compounds of formula (I), wherein $R_1$, $R_2$ and $R_3$ have meanings as defined herein above, may be prepared from amines of the formula (II)

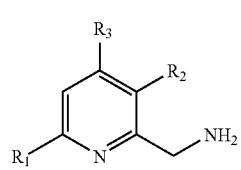

(II)

wherein $R_1$, $R_2$ and $R_3$ have meanings as defined for formula (I), using methods well-known in the art, e.g., according to methods described by Browne et al., *J. Med. Chem.*, Vol. 34, pp. 725-736 (1991) and Ahmad et al., International PCT Patent Application No. WO 01/27107, or modifications thereof.

Alternatively, compounds of formula (I), wherein $R_1$ is attached through a carbon atom, may be prepared by condensing amines of the formula (III)

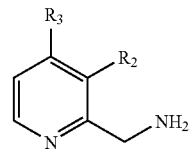

(III)

wherein $R_2$ and $R_3$ have meanings as defined herein above, with an isothiocyanate, such as phenylisothiocyanate, in an organic solvent, such as toluene or xylenes to afford thiols of the formula (IV)

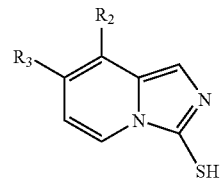

(IV)

wherein $R_2$ and $R_3$ have meanings as defined for formula (III). Amines of formula (III) are known, or if they are novel, they may be prepared according to methods well-known in the art, e.g., as described by Browne et al., supra and Ahmad et al., supra, or modifications thereof.

Thiols of formula (IV), wherein $R_2$ and $R_3$ have meanings as defined herein above, may then be treated with an alkylating agent of the formula (V)

$$R_7\text{-}Lg_1 \qquad (V)$$

wherein $R_7$ represents an alkyl group, preferably ethyl; and $Lg_1$ is a leaving group, such as chloride, bromide or iodide, preferably iodide; to afford thioethers of the formula (VI)

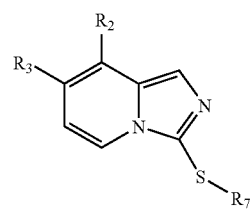

(VI)

wherein $R_2$ and $R_3$ have meanings as defined for formula (IV); and $R_7$ has a meaning as defined for formula (V); in the presence of a base, such as potassium or cesium carbonate and an organic solvent, such as acetone or acetonitrile, respectively. The alkylation reaction may be conducted at a temperature ranging from room temperature (RT) to a temperature near the boiling point of the solvent.

Thioethers of formula (VI), wherein $R_2$, $R_3$ and $R_7$ have meanings as defined herein above, may be converted to tin derivatives of the formula (VII)

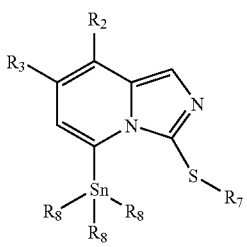

(VII)

wherein $R_2$, $R_3$ and $R_7$ have meanings as defined for formula (VI); and $R_8$ represents lower alkyl, such as methyl, ethyl or n-butyl, preferably n-butyl, by treating thioethers of formula (VI) with a base, such as n-butyllithium to form an anion, and then reacting the resulting anion with a tin reagent of the formula (VIII)

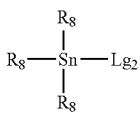

(VIII)

wherein $R_8$ has a meaning as defined for formula (VII); and $Lg_2$ represents a leaving group, such as chloride or bromide, preferably chloride. The reaction may be conducted in an inert organic solvent, such as pentane, hexane, tetrahydrofuran (THF) or ethyl ether, or in a mixture of solvents thereof, at a temperature ranging from about −45° C. to about −100° C. Preferably, the reaction is conducted in THF at a temperature of about −78° C.

Compounds of formula (VII), wherein $R_2$, $R_3$, $R_7$ and $R_8$ have meanings as defined herein above, may be coupled with a compound of the formula (IX)

$R'_1$-$Lg_3$ (IX)

wherein $R_1'$ represents $R_1$ as defined herein above; or $R_1'$ is a group convertible to $R_1$; $L9_3$ is a leaving group, such as chloride, bromide, iodide or trifluoromethanesulfonate; and $R_1'$ is attached to $Lg_3$ through a carbon atom, under conditions of Stille coupling to afford compounds of the formula (X)

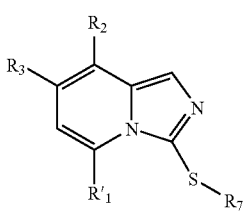

(X)

wherein $R_2$, $R_3$ and $R_7$ have meanings as defined for formula (VII); and $R_1'$ is as defined for formula (IX). For example, compounds of formula (X) may be obtained by reacting compounds of formula (VII) with a compound of formula (IX) in the presence of a palladium(0) catalyst such as tris(dibenzylidineacetone)dipalladium(0) and a ligand, such as tri-t-butylphosphine or triphenylarsine in an organic solvent, such as THF, 1,4-dioxane, N,N-dimethylformamide (DMF) or N-methylpyrrolidine (NMP). The coupling reaction may be carried out in the presence of an additive such as lithium chloride or cesium fluoride at a temperature ranging from RT to a temperature near the boiling point of the solvent.

Compounds of formula (X), wherein $R_1'$, $R_2$, $R_3$ and $R_7$ have meanings as defined herein above, may be converted to compounds of the formula (I')

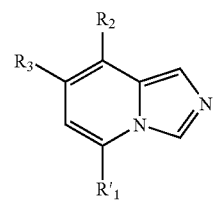

(I')

wherein $R_1'$, $R_2$ and $R_3$ have meanings as defined for formula (X), by desulfurization, e.g., in the presence of Raney nickel in a polar organic solvent, such as a lower alcohol. Preferably, the lower alcohol is ethanol, and the reaction is conducted at a temperature near the boiling point of the solvent.

The processes described herein above may be conducted under inert atmosphere, preferably under nitrogen atmosphere.

In starting compounds and intermediates which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "*Protective Groups in Organic Chemistry*", Plenum Press, London, N.Y. (1973); and Greene and Wuts, "*Protective Groups in Organic Synthesis*", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, RT or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, diastereomers, optical isomers (antipodes), racemates or mixtures thereof. The aforesaid possible isomers or mixtures thereof are within the purview of this invention.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the imidazolyl moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Finally, compounds of the invention are either obtained in the free form, as a salt thereof, or as prodrug derivatives thereof.

Compounds of the invention may be converted into acid addition salts thereof, in particular, acid addition salts with the imidazolyl moiety of the structure, preferably pharmaceutically acceptable salts thereof. These are formed, e.g., with inorganic acids, such as mineral acids, e.g., sulfuric acid, a phosphoric or hydrohalic acid, or with organic carboxylic acids, such as $(C_1-C_4)$alkanecarboxylic acids which, for example, are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, or with organic sulfonic acids, such as $(C_1-C_4)$alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

Compounds of the instant invention, provided an acidic group constitutes part of the structure, may be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

In view of the close relationship between the free compounds, the prodrug derivatives and the compounds in the form of their salts, whenever a compound is referred to in this context, a prodrug derivative and a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to inhibit aldosterone synthase, and for the treatment of conditions associated with aldosterone synthase activity. Such conditions include hypokalemia, hypertension, congestive heart failure, renal failure, in particular chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction. The said pharmaceutical compositions comprise a therapeutically effective amount of a pharmacologically active compound of the instant invention, alone or in combination with one or more pharmaceutically acceptable carriers.

The pharmacologically active compounds of the invention are useful in the manufacture of pharmaceutical compositions comprising a therapeutically effective amount thereof in conjunction or admixture with excipients or carriers suitable for either enteral or parenteral application. Preferred are tablets and gelatin capsules comprising the active ingredient together with diluents, e.g., lactose, dextrose, sucrose, mannitol, sorbitol, cellulose and/or glycine; lubricants, e.g., silica, talcum, stearic acid, its magnesium or calcium salt and/or polyethyleneglycol; for tablets also binders, e.g., magnesium aluminum silicate, starch paste, gelatin, tragacanth, methylcellulose, sodium carboxymethylcellulose and/or polyvinylpyrrolidone; if desired disintegrants, e.g., starches, agar, alginic acid or its sodium salt, or effervescent mixtures; and/or absorbants, colorants, flavors and sweeteners.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and pre-determined rate over a prolonged period of time, and means to secure the device to the skin.

The pharmaceutical formulations contain a therapeutically effective amount of a compound of the invention as defined above, either alone or in a combination with another therapeutic agent, e.g., each at an effective therapeutic dose as reported in the art. Such therapeutic agents include anti-obesity agents, such as orlistat, anti-hypertensive agents, inotropic agents and hypolipidemic agents, e.g., loop diuretics, such as ethacrynic acid, furosemide and torsemide; angiotensin converting enzyme (ACE) inhibitors, such as benazepril, captopril, enalapril, fosinopril, lisinopril, moexipril, perinodopril, quinapril, ramipril and trandolapril; inhibitors of the Na—K-ATPase membrane pump, such as digoxin; neutralendopeptidase (NEP) inhibitors; ACE/NEP inhibitors, such as omapatrilat, sampatrilat and fasidotril; angiotensin II antagonists, such as candesartan, eprosartan, irbesartan, losartan, telmisartan and valsartan, in particular, valsartan; β-adrenergic receptor blockers, such as acebutolol, atenolol, betaxolol, bisoprolol, metoprolol, nadolol, propranolol, sotalol and timolol; inotropic agents, such as digoxin, dobutamine and milrinone; calcium channel blockers, such as amlodipine, bepridil, diltiazem, felodipine, nicardipine, nimodipine, nifedipine, nisoldipine and verapamil; and 3-hydroxy-3-methyl-glutaryl coenzyme A reductase (HMG-CoA) inhibitors, such as lovastatin, pitavastatin, simvastatin, pravastatin, cerivastatin, mevastatin, velostatin, fluvastatin, dalvastatin, atorvastatin, rosuvastatin and rivastatin. A compound of the present invention may be administered either simultaneously, before or after the other active ingredient, either separately by the same or different route of administration or together in the same pharmaceutical formulation.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

Thus in an additional aspect the present invention concerns a pharmaceutical composition comprising a therapeutically effective amount of a compound of the present invention in combination with one or more pharmaceutically acceptable carriers.

In a further aspect the present invention relates to a combination, such as a combined preparation or pharmaceutical composition, respectively, comprising a compound of the invention and another therapeutic agent as described above preferably an anti-obesity agent, anti-hypertensive agent, inotropic agent or hypolipidemic agent.

For instance, the present invention concerns a pharmaceutical composition comprising a therapeutically effective amount of a compound of the invention in combination with a therapeutically effective amount of another therapeutic agent as described above preferably an anti-obesity agent, anti-hypertensive agent, inotropic agent or hypolipidemic agent.

The invention concerns furthermore;

A pharmaceutical composition or combination as described above for use as a medicament.

The use of a pharmaceutical composition or combination as described above for the preparation of a medicament for the treatment of conditions associated with aldosterone synthase activity, preferably hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction.

A pharmaceutical composition, e.g. for use in any of the conditions described above comprising a compound of the invention in free form or pharmaceutically acceptable salt form in association with a pharmaceutically acceptable diluent or carrier therefore.

A pharmaceutical composition as described above for the treatment of conditions associated with aldosterone synthase activity, preferably hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction.

A unit dosage for a mammal of about 50-70 kg may contain between about 1-1000 mg, advantageously between about 5-500 mg of the active ingredient. The therapeutically effective dosage of a compound of formula (I) is dependent on the species of warm-blooded animal (mammal), the body weight, age and individual condition, on the form of administration and on the compound involved.

The compounds of the present invention are inhibitors of aldosterone synthase, and thus may be employed for the treatment of conditions associated with aldosterone synthase activity, as described herein, e.g., hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction.

Thus, in an additional embodiment, the present invention relates to;

A compound of the present invention for use as a medicament.

The use of a compound of the invention for the preparation of a pharmaceutical composition for the prevention and/or treatment of conditions associated with aldosterone synthase activity.

A method for the prevention and/or treatment of conditions associated with aldosterone synthase activity, which comprises administering a therapeutically effective amount of a compound of the present invention.

In accordance with the foregoing the present invention provides in a yet further aspect:

A therapeutic combination, e.g. a kit, kit of parts e.g. for use in any method as defined herein, comprising a compound of the invention, in free form or in pharmaceutically acceptable salt form, to be used concomitantly or in sequence with at least one pharmaceutical composition comprising at least another therapeutic agent as described above, preferably an anti-obesity agent, antihypertensive agent, inotropic agent or hypolipidemic agent. The kit may comprise instructions for its administration.

A kit of parts comprising (i) a pharmaceutical composition of the invention, (ii) a pharmaceutical composition comprising a compound selected from an another therapeutic agent as described above preferably an anti-obesity agent, anti-hypertensive agent, inotropic agent or hypolipidemic agent, or a pharmaceutically acceptable salt thereof, in the form of two separate units of the components (i) to (ii).

A method as defined above comprising co-administration, e.g. concomitantly or in sequence, of a therapeutically effective amount of a compound of the invention in free form or in pharmaceutically acceptable salt form, and a second therapeutic agent, said second therapeutic agent being selected from the other therapeutic agents described above preferably an anti-obesity agent, anti-hypertensive agent, inotropic agent or hypolipidemic agent.

Preferably the compound of the invention is administered to a mammal in need thereof.

Preferably the compound of the invention is used for the treatment of a disease which responds to activation of conditions associated with aldosterone synthase activity.

Preferably the conditions associated with aldosterone synthase activity are selected from hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction.

A method or use according to the invention which comprises administering said compound in combination with a therapeutically effective amount of another therapeutic agent as described above preferably an anti-obesity agent, anti-hypertensive agent, inotropic agent or hypolipidemic agent.

Preferably the invention relates to; i) a use or method for the treatment of hypokalemia, hypertension, congestive heart failure, atherosclerosis, coronary heart diseases and post myocardial infarction, which method comprises administering to a mammal in need thereof a therapeutically effective amount of a compound of the invention; ii) a use or method for the treatment of restenosis, increased formation of collagen, fibrosis, and remodeling following hypertension and endothelial dysfunction, which method comprises administering to a mammal in need thereof a therapeutically effective amount of a compound of the invention; iii) a use or a method for the treatment of renal failure and nephropathy, which method comprises administering to a mammal in need thereof a therapeutically effective amount of a compound of the invention; iv) a use or a method for the treatment of syndrome X and obesity, which method comprises administering to a mammal in need thereof a therapeutically effective amount of a compound of the invention.

A method or use according to the invention which comprises administering said compound in the form of a pharmaceutical composition or combination as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests using advantageously mammals, e.g., mice, rats, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, preferably between about 1-100 mg/kg.

The activity of a compound according to the invention can be assessed by the following methods or methods well-described in the art:

The aldosterone synthase inhibitory activity in vitro may be determined as follows:

Adult male Sprague-Dawley rats weighing 125-150 g are obtained from Harlan Farms. All animals are caged in pairs and maintained under standard conditions of light and temperature. The animals are placed on a sodium depleted diet (0.01-0.02%) from Harland Teklad, Madison Wis. (Cat. No. TD90228) and maintained on normal drinking water ad libitum. The animals are maintained on this diet for two to four weeks prior to harvesting the adrenal glomerulosa cells. The rats are killed by $CO_2$ inhalation, and the adrenals are immediately removed and placed in the same ice-cold buffer used during homogenization and assay of the enzyme preparation. The adrenals are de-capsulated to obtain the glomerulosa tissue. The tissue is homogenized in a glass homogenizer containing Tris assay buffer (8.5 mM $MgCl_2$, 2.7 mM $CaCl_2$, 3.13 mM KCl, 7.59 mM NaCl, 0.1% TEA and 50 mM Tris HCl adjusted to pH 7.4). The homogenate is diluted so that 37.5 mg of glomerulosa tissue is in each mL of buffer. The homogenate is centrifuged at 4° C. at 900×g for 10 min. To start the assay, and 200 μL aliquots (450-550 μg of protein) of the adrenal cytosolic preparation is added to each glass tube containing $2.5 \times 10^{-4}$ M NADPH, $4 \times 10^{-6}$ M corticosterone. The final corticosterone concentration consisted of $4 \times 10^{-6}$ M corticosterone (C-2505, Sigma Chemical Co, St. Louis, Mo.) and $1 \times 10^{-8}$ M $[1,2,6,7-^3H]$ corticosterone (70 Ci/mM; NET 399; NEN™ Life Sciences Product, Inc., Boston, Ma.) and various concentrations of the putative aldosterone synthase inhibitor as indicated. The final volume of the incubation mixture is 0.5 mL. The mixture is incubated for 1 h at 25° C. in a Dubnoff shaking incubator at 1 atm of 95% $O_2$/5% $CO_2$. The reaction is stopped by the addition of 7 mL EtOAc, and the steroids extracted after vortexing. The water phase is extracted again with 3 mL of EtOAc. The combined extracts are dried under nitrogen, reconstituted in EtOAc, and spotted on silica gel TLC plates (LK6F; Cat. No. 4866-820; Whatman, Inc. Clifton, N.J.). The chromatograms are developed in a solvent system of toluene:acetone:water (120:80:0.8 V/v) for 60 min. The plates are scanned for radioactivity with a Bioscan System 200 Imaging Scanner (Bioscan, Ish. D.C.). The two products of the aldosterone synthase, 18—OH-corticosterone and aldosterone are scraped and counted in a liquid scintillation counter (Beckman LS6000TA, Beckman Instr., Palo Alto, Calif.).

The $IC_{50}$ values are determined from a logit-log plot (pseudo-Hill plot) according to the equation (see Pratt and Taylor, Eds, *"Principles of Drug Action"*, Churchill Livingstone Inc, NY (1990)):

$$\log P/(100-P) = n \log [I] + n \log IC_{50}$$

wherein P is the percent competition of specific binding in the presence of a given concentration of inhibitor (I). The slope (Hill Coefficient) and x intercept ($IC_{50}$) are determined by linear regression of the experimental data. The Km(app) is calculated by a computer program according to the Hanes equation (see Cornish-Bowden, Ed., "*Principles of Enzyme Kinetics*", Butterworth & Co., Boston, Mass. (1976)):

$$s/v = Km/V + s/V$$

wherein Km=Michaelis constant, V=maximum velocity, s=substrate concentration, v=velocity.

The aromatase inhibitory activity in vitro may be determined as follows:

Human placental microsome fraction is prepared from freshly delivered human term placenta as previously described with minor modifications (see Steele et al., *Steroids*, Vol. 50, pp. 147-161 (1987)). The tissue is freed of membranes and large vessels and rinsed repeatedly with 0.15 M KCl (4° C.). It is then minced in 0.25 M sucrose and homogenized. The homogenate is centrifuged at 20,000×g for 30 min. The supernatant is then centrifuged at 148,000×g for 60 min. The microsomal pellet obtained is re-suspended in 0.05 M potassium phosphate buffer pH 7.4 and centrifuged again at 148,000×g for 60 min. The resulting pellet is re-suspended in phosphate buffer, divided into aliquots, and stored at −40° C.

Human placental aromatase assay is performed in a incubation mixture consisting of: 12.5 mM phosphate buffer (12.5 mM $KH_2PO_4$, 1 mM EDTA, 1.6 mM dithiothreitol and 1.0 g/L of albumin; pH 7.5), NADPH (2.4×10$^{-4}$ M), 1β-$^{3}$H androstenedione (1×10$^{-7}$ M) and the appropriate concentration of the desired inhibitor. The assay is started by pipetting the appropriate amount 50-500 µg of the human placental microsome preparation into the incubation mixture. The mixture is incubated at 37° C. for 20 min and stopped by addition of 6 volumes of chloroform. The samples are immediately vortexed and centrifuged. The aqueous layer is carefully removed so as to avoid contamination with chloroform. The aqueous fraction is treated with an equal volume of a 5% aqueous suspension of charcoal to remove any substrate not extracted by the chloroform. After centrifugation an aliquot of the aqueous phase is counted in a liquid scintillation counter. The enzymatic activity for each concentration of inhibitor is calculated as a percent of the vehicle control, which is arbitrarily set at 100%. Therefore, the relative enzyme inhibition is expressed as a percentage: 100% minus % enzyme activity with inhibitor present.

The aldosterone synthase inhibitory activity for reduction of cardiac damage in vivo may be evaluated as follows:

The protocol is nearly identical to that previously described (see Rocha et al., *Endocrinology*, Vol. 141, pp. 3871-3878 (2000)) with minor modifications. The rats are housed in individual cages and given 0.9% NaCl as drinking fluid ad libitum throughout the experiment. Three days later rats are placed on one of the three dosing protocols. Group 1 (control) receives L-NAME for 14 days, and on day 11 of L-NAME treatment, an osmotic mini-pump containing only saline is implanted in each animal subcutaneously (s.c.). Group 2 (/L-NAME/Ang II) received L-NAME for 14 days, and on day 11 of L-NAME treatment, an osmotic mini-pump containing Ang II is implanted in each animal s.c. Group 3 (L-NAME/Ang II/test compound) is treated similarly to Group 2 but receives test compound (4 mg/kg/day) orally once a day. The test compound is dissolved in distilled water and given by gavage; whereas Groups 1 and 2 receive the vehicle. The experiment is concluded on day 14 of L-NAME treatment. The L-NAME (Sigma Chemical Co., St. Louis, Mo.) is administered in the 0.9% NaCl drinking water at a concentration of 60 mg/100 mL which results in a daily intake of approximately 60 mg/kg. Ang II is administered via Alzet osmotic mini-pumps (Model 2001; Alza Corp, Palo Alto, Calif.). The mini-pump is implanted s.c. at the nape of the neck. Ang II (human, 99% peptide purity) is purchased from Sigma Chemical Co., St. Louis, Mo. and administered at a dose of 225 µg/kg/day in saline. The concentration of Ang II used to fill the pumps is calculated based upon: (a) the mean pump rate provided by the manufacturer; (b) the body weight of the animals on the day before implantation of the pumps; and (c) dose planned. The rats are sacrificed on day 14. Their hearts are removed and sliced through the ventricle/atrium in a "bread-loaf" manner, yielding three samples from the following gross cardiac regions: superior, middle and inferior. The samples are fixed in 10% buffered formalin. Paraffin sections are cut and stained with hematoxylin/eosin. A single investigator who is blinded to the experimental groups views slides. One slide from each of three gross cardiac sample regions is analyzed per rat. Cardiac sites (left and right ventricles and the septum) are evaluated separately. The entire section is assessed histologically for the presence of myocardial damage (regardless of the severity) as evidenced by the presence of myocyte necrosis, inflammatory cells, hemorrhage and general tissue disruption. Evaluation of the histological data is made by comparing Groups 2 and 3, i.e., ANG II with or without test compound.

Illustrative of the invention, the compound of Example 1 inhibits the aldosterone synthase activity with an $IC_{50}$ value of about 50 nM.

The compounds of the present invention exhibit high affinity, selectivity, improved potency as well as good oral bioavailability, pharmacokinetic profile and safety. Furthermore, they exhibit long duration of action, long-term tolerability.

The following Examples are intended to illustrate the invention and are not to be construed as being limitations thereon. If not mentioned otherwise, all evaporations are performed under reduced pressure, preferably between about 5 and 50 mmHg. The structure of final products, intermediates and starting materials is confirmed by standard analytical methods, e.g., microanalysis, boiling point (b.p.), melting point (m.p.) and spectroscopic characteristics, e.g., MS, IR and NMR. Abbreviations used are those conventional in the art.

EXAMPLE 1

5-Naphthalen-1-yl-imidazo[1,5-a]pyridine hydrochloride

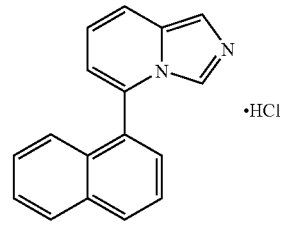

A. Imidazo[1,5-a]pyridine-3-thiol

Phenyl Isothiocyanate (22 mL, 0.184 mol) is added slowly to a solution of 2-(aminomethyl)-pyridine (19 mL, 0.184 mol) in xylenes (180 mL) with cooling on ice. The resulting solution is heated at reflux for 3 h, and then allowed to cool to RT overnight. The resulting suspension is cooled to 0° C. and the solid is collected by filtration. The solid is washed with toluene and ether, and dried under vacuum to yield imidazo[1,5-a]pyridine-3-thiol as a green solid: $^{1}$H-NMR (CDCl$_{3}$) δ 12.9 (br s, 1H), 8.25 (dd, J=7.5, 0.9, 1H), 7.21 (d, J=9.3, 1H), 7.06 (s, 1H), 6.75 (dd, J=9.3, 6.3, 1H), 6.59 (dt, J=7.5, 0.9); MS (M+1)$^{+}$ 151.

B. 3-Ethylsulfanyl-imidazo[1,5-a]pyridine

A 250 mL round-bottom flask is charged with acetone (92 mL), the title A compound, imidazo[1,5-a]pyridine-3-thiol (21.26 g, 0.141 mol), potassium carbonate (39.14 g, 0.283 mol) and ethyl iodide (12.4 mL, 0.155 mol). The resulting suspension is heated at 45° C. for 12 h. The reaction is cooled to RT and filtered. The solid is washed with acetone and the filtrate is concentrated under reduced pressure. The residue is dissolved in methylene chloride and filtered. The filtrate is concentrated under reduced pressure and the residue is distilled under vacuum through a 6 cm Vigreux column to yield 3-ethylsulfanyl-imidazo[1-5a]pyridine (b.p. 168-172 at 2.1 mmHg) as a yellow oil: $^1$H-NMR (CDCl$_3$) δ 8.18 (dd, J=6.6, 0.6, 1H), 7.52 (s, 1H), 7.43 (d, J=9.0, 1H), 6.76 (dd, J=9.0, 6.3 1H), 6.64 (app. t, J=6.3, 1H), 2.95 (q, J=7.2, 2H), 1.25 (t, J=7.2, 3H); MS (M+1)$^+$ 179.

C. 3-Ethylsulfanyl-5-tributylstannyl-imidazo[1,5-a]pyridine n-Butyllithium (1.6 M, 4.2 mL, 6.7 mmol) is added slowly to a solution of the title B compound, 3-ethylsulfanyl-5-methyl-imidazo[1,5-a]pyridine (1.14 g, 6.4 mmol) in anhydrous THF (7 mL) at −78° C. The resulting solution is stirred at −78° C. for 1 h and tributyltinchloride (2.0 mL, 7.4 mmol) is added. The reaction is stirred at −78° C. for 1 h further, and then allowed slowly to warm to RT overnight. The reaction is quenched by addition of saturated aqueous ammonium chloride (15 mL) and the mixture is extracted two times with ethyl acetate. The organic extracts are combined, washed with aqueous potassium fluoride solution (3 M, 20 mL), dried over anhydrous magnesium sulfate, filtered and concentrated. The residue is purified by flash column chromatography on silica using 10% ethyl acetate in hexanes as the eluant to yield 3-ethylsulfanyl-5-tributylstannyl-imidazo[1,5-a]pyridine as a dark oil: $^1$H-NMR (CDCl$_3$) δ 7.51 (s, 1H), 7.38 (dd, J=8.7, 1.2, 1H), 6.71 (dd, J=6.3, 1.5, 1H), 6.63 (dd, J=8.7, 6.3, 1H), 2.98 (q, J=7.4, 2H), 1.58-1.48 (m, 6H), 1.40-1.17 (m, 15H), 0.88 (t, J =7.5, 9H); $^{13}$C-NMR (CDCl$_3$) δ 140.27, 133.53, 132.20, 124.88, 124.76, 124.63, 121.89, 118.77, 118.65, 118.56, 32.22, 29.66, 29.37, 29.30, 29.22, 27.94, 27.79, 27.68, 27.42, 15.59, 15.52, 14.83, 14.12, 14.03, 12.71, 12.65; MS (M+1)$^+$ 465, 466, 467, 468, 469 (tin isotope pattern).

D. 3-Ethylsulfanyl-5-naphthalen-1-yl-imidazo[1,5-a]pyridine

To a solution of the title C compound, 3-ethylsulfanyl-5-tributylstannyl-imidazo-[1,5-a]pyridine (550 mg, 1.18 mmol) in 1,4-dioxane (8 mL), 1-bromonaphthalene (0.18 mL, 1.29 mmol) is added followed by tris(dibenzylidineacetone)dipalladium(0) (38 mg, 0.041 mmol), tri-t-butylphosphine (80 μL, 0.329 mmol) and cesium fluoride (396 mg, 2.6 mmol). The suspension is heated at 100° C. under nitrogen in a sealed tube for two days. The mixture is cooled, diluted with ethyl ether and filtered through a short silica plug. The solvent is evaporated under reduced pressure, and the residue is purified by flash column chromatography on silica using 10% ethyl acetate in hexanes to yield 3-ethylsulfanyl-5-naphthalen-1-yl-imidazo[1,5-a]pyridine as an amber oil: $^1$H-NMR (CDCl$_3$) δ 8.01 (dd, J=7.5, 1.8, 1H), 7.93 (d, J=8.1, 1H), 7.61 (s, 1H), 7.58-7.47 (m, 4H), 7.41-7.32 (m, 2H), 6.78 (dd, J=9.0, 6.6, 1H), 6.51 (dd, J=6.6, 1.2, 1H), 2.66 (q, J=7.2, 2H), 0.86 (t, J=7.2, 3H), MS (M+1)$^+$ 305.

E. 5-Naphthalen-1-yl-imidazo[1,5-a]pyridine hydrochloride

Raney Nickel suspension (1 mL, Fluka Cat. No. 83440) is added to a solution of the title D compound, 3-ethylsulfanyl-5-naphthalen-1-yl-imidazo[1,5-a]pyridine (268 mg, 0.88 mmol) in ethanol (15 mL) and heated at reflux overnight. Additional Raney Nickel (1 mL) is added, and the reaction mixture is heated at reflux for three days further, until MS showed complete disappearance of the starting material. The catalyst is filtered off and washed with ethanol. The combined filtrates are concentrated under reduced pressure. The residue is purified by flash column chromatography on silica using ethyl ether as the eluant to yield 5-naphthalen-1-yl-imidazo[1,5-a]pyridine as an amber film. The hydrochloride salt is prepared in acetone by addition of an ethereal solution of HCl (1.2 eq.). The resulting precipitate is re-crystallized from acetonitrile to yield 5-naphthalen-1-yl-imidazo[1,5-a]pyridine hydrochloride (m.p.222-223° C.): $^1$H-NMR, (MeOH-d$_4$) δ 8.71 (s, 1H), 8.21 (d, J=8.1, 1H), 8.16 (s, 1H), 8.13 (d, J=16.3, 1H), 8.04 (d, J=17, 1H), 7.98-7.70 (m, 2H), 7.61 (dt, J=5.6,1.2, 1H); 7.53-7.40, m, (3H); 7.28 (d, J=7.7, 1H); $^{13}$C-NMR (MeOH-d$_4$) δ 135.8, 135.53, 132.84, 132.68, 131.96, 130.34, 130.13, 129.81, 129.11, 128.15, 127.04, 126.18, 125.60, 124.79, 120.93, 119.43, 116.50, 112.96; MS (M+1)$^+$ 245.

EXAMPLE 2

5-Biphenyl-4-yl-imidazo[1,5-a]pyridine hydrochloride

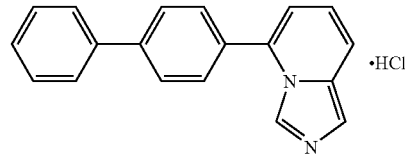

The title compound is prepared analogously to Example 1 (m.p. 240-242° C.): $^1$H-NMR (MeOH-d$_4$) δ 9.43 (s, 1H), 8.14 (d, J=1.5, 1H), 7.93-7.82 (m, 5H), 7.74-7.71 (m, 2H), 7.53-7.47 (m, 2H), 7.44-7.37 (m, 2H), 7.19 (dd, J=6.0, 0.9,1 H); $^{13}$C-NMR (MeOH-d$_4$) δ 145.11, 141.09, 137.29, 132.94, 131.80, 130.29, 130.19, 129.32, 128.16, 126.36, 125.42, 119.26, 118.84, 112.72; MS (M+1)$^+$ 271.

EXAMPLE 3

5-Biphenyl-2-yl-imidazo[1,5-a]pyridine hydrochloride

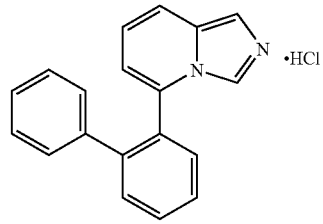

The title compound is prepared analogously to Example 1 (m.p. 200-201° C.): $^1$H-NMR (MeOH-d$_4$) δ 8.75 (s, 1H), 7.86 (d, J=1.3, 1H), 7.79-7.35 (m, 2H), 7.69-7.62 (m, 3H), 7.33 (dd, J=6.8,2.4, 1H), 7.26-7.21 (m, 3H); 7.17-7.12 (m, 3H); $^{13}$C-NMR (MeOH-d$_4$) δ 142.64, 140.92, 137.14, 132.71, 132.32, 132.23, 131.95, 131.18, 129.94, 129.58, 129.26, 129.14, 129.04, 125.91, 125.70, 121.22, 118.73, 112.49; MS (M+1)$^+$ 271.

EXAMPLE 4

5-Benzofuran-3-yl-imidazo[1,5-a]pyridine hydrochloride

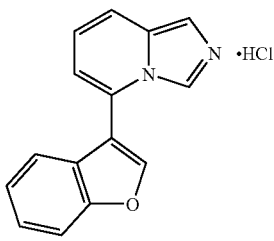

The title compound is prepared analogously to Example 1 (m.p. 96-98° C.): $^1$H-NMR (MeOH-d$_4$) δ 9.40 (s, 1H), 8.48 (s, 1H), 8.15 (s, 1H), 7.93 (dd, J=9.0, 1H), 7.72 (d, J=6.0, 1H), 7.58 (d, J=9.0, 1H), 7.50 (t, J=6.0, 1H), 7.41 (m, 3H); MS (M+1)$^+$ 234.

EXAMPLE 5

4-Imidazo[1,5-a]pyridin-5-yl-3,6-dihydro-2H-pyridine-1-carboxylic acid benzyl ester hydrochloride

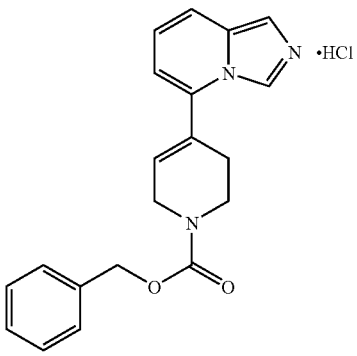

The title compound is prepared analogously to Example 1 (m.p. 149-152° C.): $^1$H-NMR (MeOH-d$_4$) δ 8.08 (s, 1H), 7.80 (d, J=7.3, 1H), 7.39-7.29 (m, 5H), 7.05 (d, J=5.8, 1H), 6.41 (s, 1H), 5.19 (s, 2H), 4.28 (s, 2H), 3.83 (s, 2H), 2.60 (s, 2H); MS (M+1)$^+$ 333.

EXAMPLE 6

4-Imidazo[5,1-a]isoquinolin-5-yl-benzoic acid ethyl ester hydrochloride

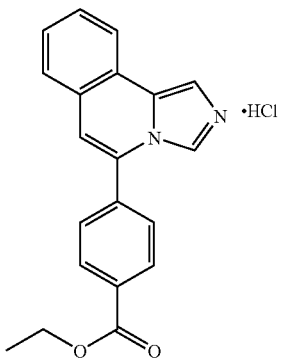

The title compound is prepared analogously to Example 1: $^1$H-NMR (CDCl$_3$) δ 8.24 (d, J=8.1, 2H), 8.07 (d, J=6.4, 2H), 7.93 (s, 1H), 7.77 (d, J=8.1, 2H), 7.63 (d, J=7.7, 1H), 7.56 (t, J=7.4, 1H), 7.46 (t, J=7.3, 1H), 6.8 (s, 1H), 4.45 (q, J=7.1, 2H), 1.45 (t, J=7.1, 3H); MS (M+1)$^+$ 316.

What is claimed is:

1. A method for the treatment of hypertension in a mammal in need thereof through the inhibition of aldosterone synthase activity, comprising:
   administering to the mammal in need thereof a therapeutically effective amount of a compound of formula (I)

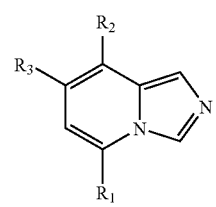

(I)

wherein
   $R_1$ is cycloalkyl, heterocyclyl or an aryl radical of the formula

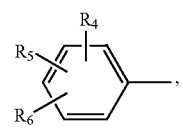

in which
   $R_4$ is cycloalkyl, aryl or heterocyclyl; or
   $R_4$ is optionally substituted alkyl, alkoxy, hydroxy, halogen or trifluoromethyl provided that both $R_5$ and $R_6$ are not hydrogen;
   $R_5$ is hydrogen, halogen, cyano, alkoxy or trifluoromethyl; or
   $R_4$ and $R_5$ combined together with the carbon atoms to which they are attached form an optionally substituted aromatic or heteroaromatic 5- or 6-membered ring provided that $R_4$ and $R_5$ are attached to carbon atoms adjacent to each other; or
   $R_4$ and $R_5$ combined are alkylene which taken together with the carbon atoms to which they are attached form a 4- to 7-membered ring provided that $R_4$ and $R_5$ are attached to carbon atoms adjacent to each other;
   $R_6$ is hydrogen, halogen, cyano, nitro, trifluoromethyl, optionally substituted lower alkyl, optionally substituted amino, alkoxy, carboxy, alkoxycarbonyl, sulfonyl or carbamoyl;
   $R_2$ and $R_3$ are, independently, hydrogen, trifluoromethyl or alkoxy; or
   $R_2$ and $R_3$ combined together with the carbon atoms to which they are attached form an optionally substituted aromatic or heteroaromatic 5- or 6-membered ring; or
   $R_2$ and $R_3$ combined are alkylene which taken together with the carbon atoms to which they are attached form a 4- to 7-membered ring;
or a pharmaceutically acceptable salt thereof.

2. A method for the treatment of hypertension through inhibition of aldosterone synthase activity in a mammal in need thereof, comprising:
   administering to the mammal in need thereof a therapeutically effective amount of a compound of formula (IB)

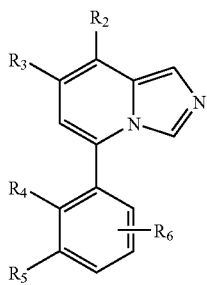

wherein
- $R_2$ and $R_3$ are, independently, hydrogen, trifluomethyl or alkoxy; or
- $R_2$ and $R_3$ combined together with the carbon atoms to which they are attached form aromatic or heteroaromatic 5- to 6-membered ring;
- $R_4$ is cycloalkyl, aryl or heterocyclyl; or
- $R_4$ is hydroxy, halogen or trifluoromethyl provided that both $R_5$ and $R_6$ are not hydrogen;
- $R_5$ is hydrogen, halogen, cyano, alkoxy or trifluoromethyl; or
- $R_4$ and $R_5$ combined together with the carbon atoms to which they are attached form an optionally substituted aromatic or heteroaromatic 5- or 6-membered ring;
- $R_6$ is hydrogen, halogen, cyano, nitro, trifluoromethyl, optionally substituted lower alkyl, optionally substituted amino, alkoxy, carboxy, alkoxycarbonyl, sulfonyl or carbamoyl;

or a pharmaceutically acceptable salt thereof.

3. The method according to claim 1, wherein the compounds is further defined by
- $R_1$ is heterocyclyl;
- $R_2$ and $R_3$ are hydrogen;
or pharmaceutically acceptable salt thereof.

4. The method according to claim 2, wherein the compound is further defined by
- $R_2$ and $R_3$ are hydrogen;
or a pharmaceutically acceptable salt thereof.

5. The method according to claim 2, wherein the compound is further defined by $R_4$ is monocyclic aryl or heteroaryl;
- $R_5$ is hydrogen;
- $R_6$ is hydrogen, halogen, cyano, trifluoromethyl or alkoxy;
or a pharmaceutically acceptable salt thereof.

6. The method according to claim 2, wherein the compound is further defined by
- $R_4$ and $R_5$ combined together with the carbon atoms to which they are attached form an optionally substituted aromatic or heteroaromatic 5- or 6-membered ring;
- $R_6$ is hydrogen, halogen, cyano, trifluoromethyl or alkoxy;
or a pharmaceutically acceptable salt thereof.

7. The method according to claim 1, wherein the compound is
- 5-Naphthalen-1-yl-imidazo[1,5-a]pyridine;
- 5-Biphenyl-4-yl-imidazo[1,5-a]pyridine;
- 5-Biphenyl-2-yl-imidazo[1,5-a]pyridine;
- 5-Benzofuran-3-yl-imidazo[1,5-a]pyridine; and
- 4-imidazo[1,5-a]pyridin-5-yl-3,6-dihydro-2H-pyridine-1-carboxylic acid benzyl ester;

or a pharmaceutically acceptable salt thereof.

8. A pharmaceutical composition, comprising:
a therapeutically effective amount of a compound of formula (I)

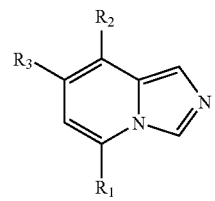

wherein
$R_1$ is cycloalkyl, heterocyclyl or an aryl radical of the formula

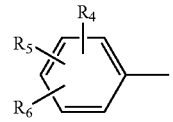

in which
- $R_4$ is cycloalkyl, aryl or heterocyclyl; or
- $R_4$ is optionally substituted alkyl, alkoxy, hydroxy, halogen or trifluoromethyl provided that both $R_5$ and $R_6$ are not hydrogen;
- $R_5$ is hydrogen, halogen, cyano, alkoxy or trifluoromethyl; or
- $R_4$ and $R_5$ combined together with the carbon atoms to which they are attached form an optionally substituted aromatic or heteroaromatic 5- or 6-membered ring provided that $R_4$ and $R_5$ are attached to carbon atoms adjacent to each other; or
- $R_4$ and $R_5$ combined are alkylene which taken together with the carbon atoms to which they are attached form a 4- to 7-membered ring provided that $R_4$ and $R_5$ are attached to carbon atoms adjacent to each other;
- $R_6$ is hydrogen, halogen, cyano, nitro, trifluoromethyl, optionally substituted lower alkyl, optionally substituted amino, alkoxy, carboxy, alkoxycarbonyl, sulfonyl or carbamoyl;
- $R_2$ and $R_3$ are, independently, hydrogen, trifluoromethyl or alkoxy; or
- $R_2$ and $R_3$ combined together with the carbon atoms to which they are attached form an optionally substituted aromatic or heteroaromatic 5- or 6-membered ring; or
- $R_2$ and $R_3$ combined are alkylene which taken together with the carbon atoms to which they are attached form a 4- to 7-membered ring;

or a pharmaceutically acceptable salt thereof; alone or in combination with one ore more pharmaceutically acceptable carriers.

* * * * *